(12) United States Patent
Jago et al.

(10) Patent No.: US 6,458,083 B1
(45) Date of Patent: Oct. 1, 2002

(54) ULTRASONIC HARMONIC IMAGING WITH ADAPTIVE IMAGE FORMATION

(75) Inventors: James R. Jago, Seattle, WA (US); David N. Roundhill, Bothell, WA (US); Jeffry E. Powers, Bainbridge Is., WA (US); Michalakis Averkiou, Kirkland, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/518,348

(22) Filed: Mar. 3, 2000

Related U.S. Application Data

(60) Continuation-in-part of application No. 09/247,343, filed on Feb. 8, 1999, which is a division of application No. 08/943,546, filed on Oct. 3, 1997, now Pat. No. 5,879,303.
(60) Provisional application No. 60/032,771, filed on Nov. 26, 1996.

(51) Int. Cl.$^7$ ................................................. A61B 8/00
(52) U.S. Cl. ........................................ 600/443; 600/458
(58) Field of Search ................................ 600/437, 443, 600/447, 458

(56) References Cited

U.S. PATENT DOCUMENTS

| | | |
|---|---|---|
| 4,702,258 A | 10/1987 | Nicolas |
| 4,714,846 A | 12/1987 | Pesque |
| 5,158,071 A | 10/1992 | Umemura |
| 5,255,683 A | 10/1993 | Monaghan |
| 5,410,516 A | 4/1995 | Uhlendorf et al. |
| 5,415,171 A | 5/1995 | Goh |
| 5,419,328 A | 5/1995 | Goh |
| 5,435,311 A | 7/1995 | Umemura |
| 5,608,690 A | 3/1997 | Hossack et al. |
| 5,720,289 A | 2/1998 | Wright et al. |
| 5,740,128 A | 4/1998 | Hossack et al. |
| 5,879,303 A | 3/1999 | Averkiou et al. |
| 5,882,306 A | 3/1999 | Ramamurthy et al. |
| 5,897,500 A | 4/1999 | Zhao |
| 5,957,852 A * | 9/1999 | Hossack et al. ............ 600/447 |
| 5,961,460 A | 10/1999 | Guracar et al. |
| 5,961,464 A * | 10/1999 | Poland ........................ 600/458 |
| 6,120,448 A * | 9/2000 | Bradley et al. ............. 600/443 |
| 6,132,377 A * | 10/2000 | Bolorforosh et al. ....... 600/458 |

FOREIGN PATENT DOCUMENTS

| | | |
|---|---|---|
| WO | WO 98/20361 A1 | 5/1998 |
| WO | WO 98/46139 | 10/1998 |
| WO | WO 98/57583 | 12/1998 |
| WO | WO 99/05969 | 2/1999 |

OTHER PUBLICATIONS

Starritt, Evidence for ultrasonic finite amplitude distortion in muscle using medical equipment, JASA 77(1), Jan. 1985 at 302–06.

(List continued on next page.)

*Primary Examiner*—Francis J. Jaworski
(74) *Attorney, Agent, or Firm*—W. Brinton Yorks, Jr.

(57) ABSTRACT

An ultrasonic diagnostic imaging system receives fundamental frequency, harmonic contrast, and tissue harmonic echo information for image processing. The fundamental and harmonic signal content of the echo information is analyzed and the relative content of an output signal is adjusted as necessary to take advantage of the different characteristics of the different types of echo information present in the echo signal. The ultrasound system can produce images which are an adaptive blend of fundamental, tissue harmonic and harmonic contrast echo information.

25 Claims, 3 Drawing Sheets

OTHER PUBLICATIONS

Muir, Prediction of nonlinear acoustic effects at biomedical frequencies and intensities, Ult. in Med. & Biol., Bol. 6 at 345–57 (1980).

Carstensen, Demonstration of nonlinear acoustical effects at biomedical frequencies and intensities, Ult. in Med. & Biol. vol. 6 at 359–68 (1980).

Starritt, The development of harmonic distortion in pulsed finite–amplitude ultrasound passing through liver, Phys. Med. Biol., vol. 31, No. 12, 1401–09 (1986).

Ward, Non–linear propagation applied to the improvement of lateral resolution in medical ultrasound scanners, 1995 World Cong. on Ult. at 965–68.

Law, Ultrasonic determination of the nonlinearity parameter B/A for biological media, JASA 69(4), Apr. 1981 at 1210–12.

Dunn, et al., Nonlinear Ultrasonic Wave Propagation in Biological Materials, 1981 Ultrasonics Symposium at 527–32 (IEEE).

Muir, Nonlinear Effects in Acoustic Imaging, Acoustical Imaging, vol. 9 at 93–109 (Plenum Press, NYC, 1980).

Ichida et al., Imaging the Nonlinear Parameter of a Medium, Ultrasonic Imaging, vol. 5 at 295–99 (Academic Press, 1983).

Christopher, Finite Amplitude Distortion–Based Inhomogeneous Pulse Echo Ultrasonic Imaging, IEEE Tras. Ult., Ferro & Freq. Contr., vol. 44, Jan. 1997 at 123 and particularly p. 138.

Burns et al., Harmonic Power Mode Doppler Using Microbubble Contrast Agents, J.E.M.U., vol. 16, No. 4 at 132–42 (Masson, Paris, 1995).

Burns, et al., Harmonic Imaging Principles and Preliminary Results, Angiology, vol. 47, No. 7. Part 2 at 563–574 (Jul. 1996 New York).

Burns, Presentation of Papers Nos. 241, 243, 1046, 1438, 1682, 166, 169 Supplements to Radiology (Nov. 1992, vol. 185, Nov. 1993, vol. 193, Nov. 1995, vol. 197, Nov. 1996, vol. 201).

Averkiou, et al., Measurements of Harmonic Generation in a Focused Finite–Amplitude Sound Beam, J. Acoust. Soc. Am. 98(6) at 3439–42 (Dec. 1995).

Ward, et al., Nonlinear Propagation Applied to the improvement of Resolution in Diagnostic Medical Ultrasound, J. Acoust. Soc. Am. 101(1) at 143–54 (Jan. 1997), particularly p. 143.

Schrope, et al., Simulated Capillary Blood Flow Measurement Using a Nonlinear Ultrasonic Contrast Agent, Ultrasonic Imaging 13 at 134–58 (Acu. Press 1992).

Schrope, et al., Second Harmonic Ultrasonic Blood Perfusion Measurement, Ult. in Med. & Biol. 19(7) at 567–79 (Pergamon Press 1993).

* cited by examiner

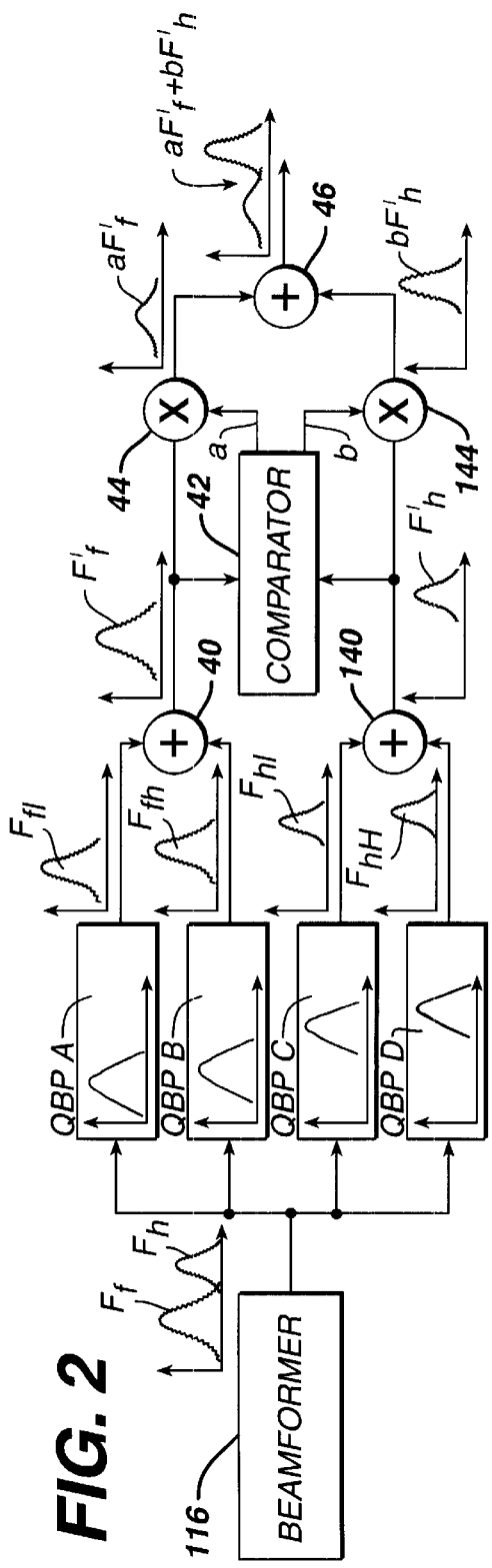
FIG. 2
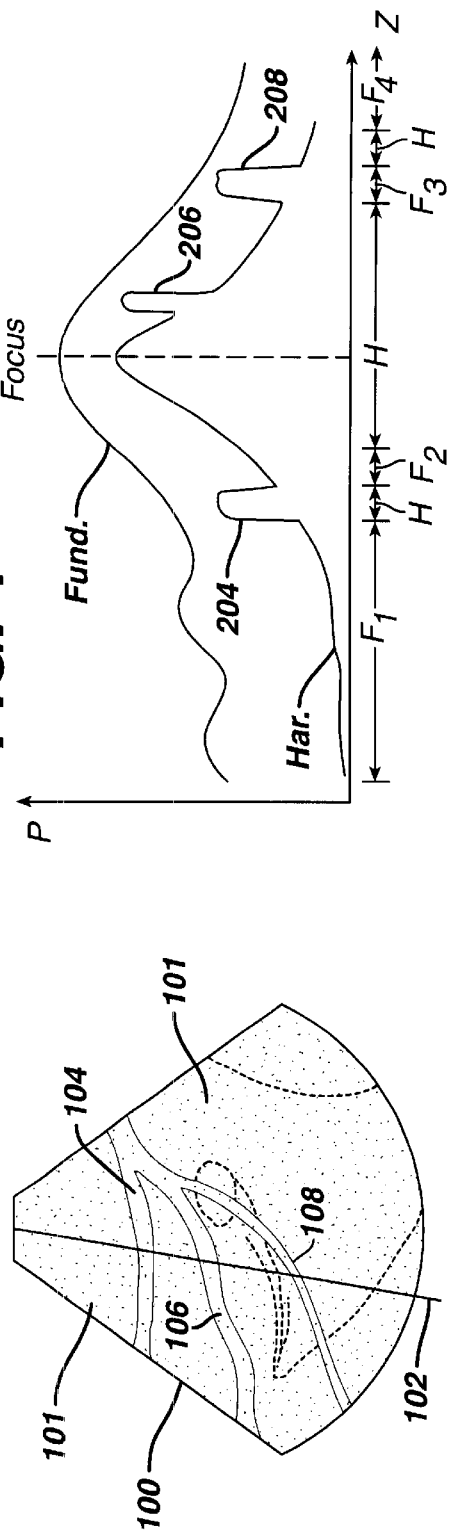
FIG. 4
FIG. 3

ULTRASONIC HARMONIC IMAGING WITH ADAPTIVE IMAGE FORMATION

This is a continuation-in-part of U.S. patent application Ser. No. 09/247,343 filed Feb. 8, 1999, which is a division of U.S. patent application Ser. No. 08/943,546 filed Oct. 3, 1997, now U.S. Pat. No. 5,879,303, which claims the benefit of U.S. Provisional Application No. 60/032,771 filed Nov. 26, 1996.

This invention relates to ultrasonic diagnostic imaging systems and, in particular, to ultrasonic diagnostic imaging systems which produce images of acquired harmonic signals.

The use of ultrasonic signals which are harmonically related to transmitted ultrasound signals for ultrasonic diagnostic imaging is described in U.S. Pat. No. 5,833,613 (Averkiou et al.) and U.S. Pat. No. 5,879,303 (Averkiou et al.) The '613 patent describes a number of techniques for imaging with harmonic contrast agents. Ultrasonic contrast agents are comprised of tiny encapsulated microbubbles which, when struck by a transmitted ultrasound wave, will exhibit nonlinear resonance, including resonance at harmonic frequencies of the transmitted wave frequency. This nonlinear resonance will return an echo signal containing the harmonic frequencies in addition to components at the fundamental (transmit) frequency. While the harmonic components are not as great in intensity as the fundamental components, they are nonetheless of relatively significant intensity and can be readily detected and discriminated to provide segmented contrast signal information.

The '303 patent describes another form of ultrasonic harmonic imaging known as tissue harmonic imaging. Tissue harmonic imaging relies upon the distortion of a transmitted wave which occurs as the wave passes through the tissue of the body. This distortion gives rise to nonlinear signal components including those at harmonics of the fundamental transmit frequency. The tissue harmonic signal components are of a lesser relative intensity as compared to contrast harmonic signal components, but may nonetheless be readily detected and used to form ultrasonic images. As explained in the '303 patent, tissue harmonic imaging prevents the occurrence of nearfield and other image artifacts which are common to fundamental signal images.

In both contrast and tissue harmonic imaging, the echo signals received can contain both harmonic signal components and fundamental frequency components. These signal components can vary with the type of imaging procedure being performed and the sources of the echo signals. For example, harmonic contrast echo signal components are usually of a lesser intensity than the fundamental echo components, and tissue harmonic signals are generally of a lesser intensity than harmonic contrast components. Fundamental and harmonic contrast components are generally stronger for echoes returned from shallower depths, whereas tissue harmonic components require the passage of a transmit pulse through tissue before the harmonic components develop. All three types of echo signals are subject to depth dependent intensity attenuation and depth dependent frequency attenuation.

The aforementioned '303 patent takes advantage of these differing characteristics by teaching how produce images which are a blend of fundamental and harmonic signals at different depths and image areas. It would be desirable for such blended images to be formed adaptively in response to actual signal conditions, so that even greater advantage and hence even better images can be formed from fundamental, harmonic contrast, and tissue harmonic signal information.

In accordance with the principles of the present invention, an apparatus and technique are described for adaptively forming images from linear (fundamental) and nonlinear (harmonic) echo information. The fundamental and harmonic content of an echo signal is detected and used to form a composite signal of fundamental and/or echo information which is a function of the relative quality of the two components of the echo signal. In a preferred embodiment the technique is performed on speckle reduced image information. Images are thus formed from fundamental, harmonic contrast, and tissue harmonic signal information which use the respective signal components to maximal advantage and thus higher quality and more diagnostic images.

In the drawings:

FIG. 2 illustrates in block diagram form an adaptive technique for blending fundamental and harmonic signals in an image in accordance with the principles of the present invention;

FIG. 3 shows an ultrasound image with blood vessels carrying an ultrasonic contrast agent;

FIG. 4 illustrates examplary fundamental and harmonic responses from echoes received along a scanline of the image of FIG. 3.

Figure 1:
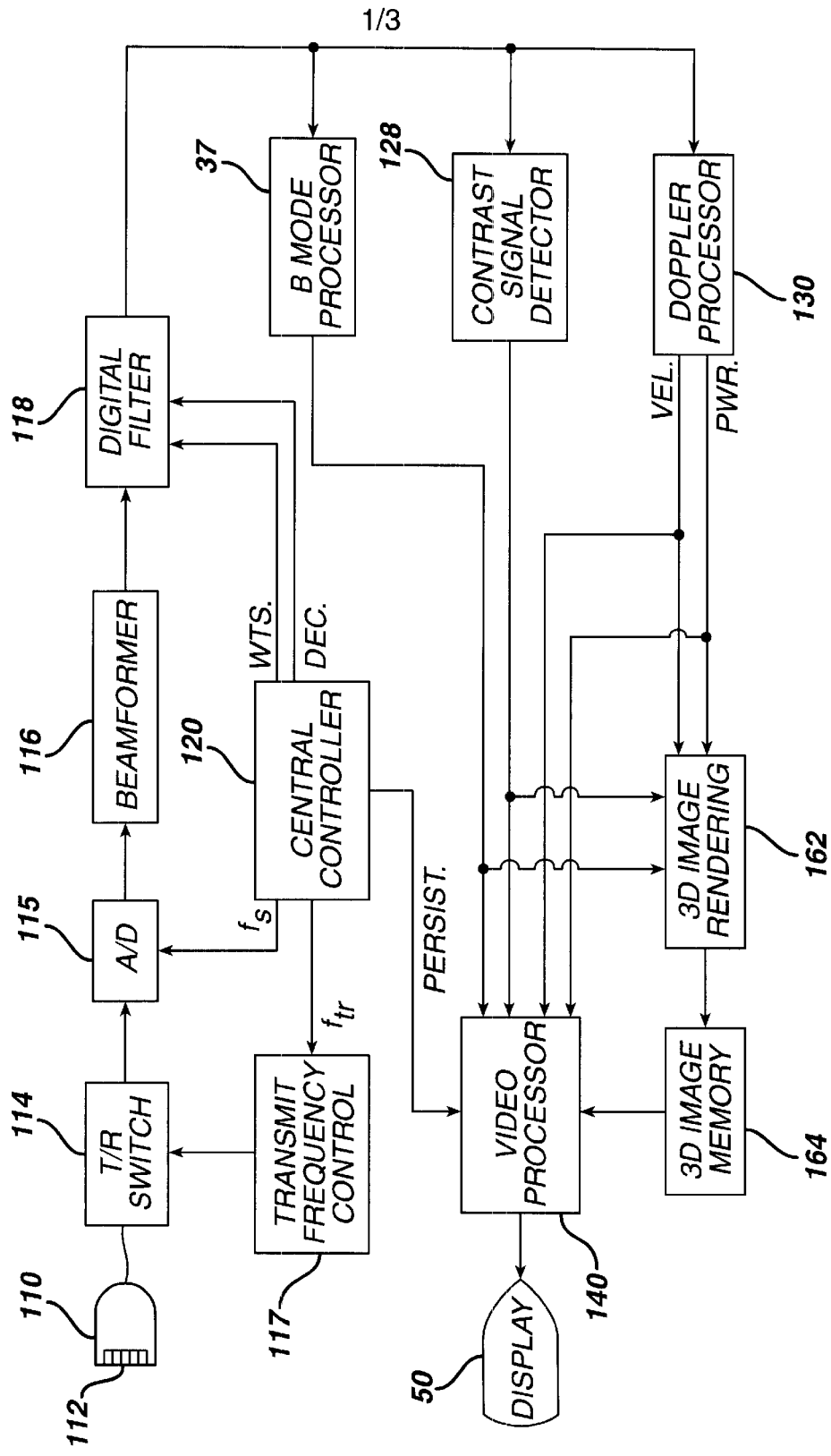
FIG. 1 illustrates in block diagram form an ultrasonic harmonic imaging system constructed in accordance with the principles of the present invention.

Referring first to FIG. 1, an ultrasonic imaging system for harmonic imaging is shown in block diagram form. A central controller 120 commands a transmit frequency control 117 to transmit a desired transmit frequency band. The parameters of the transmit frequency band, $f_{tr}$, are coupled to the transmit frequency control 117, which causes the transducer 112 of ultrasonic probe 110 to transmit ultrasonic waves in the fundamental frequency band. The array transducer 112 of the probe 110 transmits ultrasonic energy and receives echoes returned in response to this transmission. The response characteristic of the transducer can encompass one broad passband or two distinguishable passbands, one around the fundamental transmit frequency and another about a harmonic frequency in the received passband. For harmonic imaging, a broadband transducer having a passband encompassing both the transmitted fundamental and received harmonic passbands is preferred. In harmonic contrast imaging the echo signals returned from harmonic contrast agents include harmonics of the fundamental transmit band. In tissue harmonic imaging tissue and cells in the body alter the transmitted fundamental frequency signals during propagation and the returned echoes contain harmonic components of the originally transmitted fundamental frequency. In FIG. 1 these echoes are received by the transducer array 112, coupled through the T/R switch 114 and digitized by analog to digital converters 115. The sampling frequency $f_s$ of the A/D converters 115 is controlled by the central controller. The desired sampling rate dictated by sampling theory is at least twice the highest frequency of the received passband. Sampling rates higher than the minimum requirement are preferable, such as 24, 32, or 40 MHz.

The echo signal samples from the individual transducer elements are delayed and summed by a beamformer 116 to form coherent echo signals. The digital coherent echo signals are then filtered by a digital filter 118. The digital filter 118 can bandpass filter the signals to separate signals of the desired harmonic passband, and can also shift the frequency band to a lower or baseband frequency range. A preferred filter can take the form of a multitap digital FIR filter which can also decimate the output data rate. The digital filter 118 can also separate harmonic and fundamental frequency components by combining spatially correlated echoes which have been produced by differently modulated transmit signals, a technique known as pulse inversion which is described in U.S. Pat. No. 5,951,478. A digital filter of either type can be programmed to pass received fundamental frequencies at one moment, and harmonic frequencies at the next. The digital filter can thus be operated to alternately produce images or lines of fundamental and harmonic digital signals, or lines of different alternating harmonics in a time-interleaved sequence simply by changing the filter coefficients of an FIR filter or the sense in which multiple echoes are combined in pulse inversion.

The filtered echo signals from the tissue or contrast agent are processed by either a B mode processor 37, a contrast signal processor 128, or a Doppler processor 130 for display as a two dimensional ultrasonic image on the display 50. A preferred form for the contrast signal processor is the power motion imaging processor shown and described in U.S. Pat. No. 5,718,229. Details of harmonic Doppler processing are found in U.S. Pat. No. 6,036,643. Harmonic contrast and tissue harmonic signals may be processed for display by any of the three processors 37, 128 and 130, as may fundamental frequency signals. The outputs of these processors are coupled to a 3D image rendering processor 162 for the rendering of three dimensional images, which are stored in a 3D image memory 164. Three dimensional rendering may be performed as described in U.S. Pat. Nos. 5,720,291, 5,474,073 and 5,485,842. The signals from the contrast signal detector 128, the processors 37 and 130, and the three dimensional image signals are coupled to a video processor 140 where they may be selected for two or three dimensional display on an image display 50 as dictated by user selection.

In accordance with the principles of the present invention, the harmonic and fundamental signal content of an ultrasound image is adaptively varied as a function of the received signals. A processor which provides this adaptive capability is shown in FIG. 2. The beamformer 116 is shown producing fundamental and harmonic signals $F_f$ and $F_h$ in the spectrum drawn at the output of the beamformer. In this example the signals of these two spectra are both significant enough to form either a fundamental signal image or a harmonic image. These signals are coupled to the inputs of four quadrature bandpass filters (QBPs) labeled A, B, C, and D. The QBPs perform quadrature demodulation of the I and Q signal components of the echo signals and also filter the signals through a programmable filter passband. The QBPs in this embodiment also perform detection using the I and Q components and separately detect the fundamental and harmonic frequency bands. The QBPs may be formed by digital FIR filters as more particularly described in U.S. Pat. No. 5,879,303. Alternatively, or in addition, fundamental and harmonic separation can be performed by the technique known as pulse inversion prior to the QBP filters, with the fundamental components applied to QBP A and QBP B, and the harmonic components applied to QBP C and QBP D. When the echoes from two oppositely phase transmit signals are summed, the harmonic components are produced and applied to QBPs C and D, and when the same echoes are subtractively combined the fundamental components are produced and can be applied to QBPs A and B.

As indicated by the passband characteristics shown for the four QBP filters, the passbands of QBPs A and B are different from each other, as are the passbands of QBPs C and D. This passband differentiation allows the echo signals in the respective passbands to be speckle reduced by frequency compounding. The QBP A produces fundamental signals in a low frequency passband $F_{fL}$, and the QBP B produces fundamental signals in a high frequency passband $F_{fH}$. When the signals in these two passband are separately detected and combined, the speckle in the fundamental signals is reduced by frequency compounding, as more particularly described in U.S. Pat. No. 5,879,303.

Likewise, the QBP C produces fundamental signals in a low frequency passband $F_{hL}$, and the QBP D produces fundamental signals in a high frequency passband $F_{hH}$. When the signals in these two passband are separately detected and combined, the speckle in the harmonic signals is reduced by frequency compounding. By these processes speckle reduced fundamental signals $F_f'$ are produced at the output of adder 40, and speckle reduced harmonic signals $F_h'$ are produced at the output of adder 140.

A comparator 42 then compares the fundamental and harmonic signals and producing scaling factors a and b as a result of the comparison. For example the comparator 42 can compare the respective amplitudes of the harmonic and fundamental signals at each sample point along a received scanline. The scaling factors a and b are then used to scale the respective contributions of the fundamental and harmonic signals in a composite output signal. The scaling factors can, if desired, be normalized so that b=1−a at all times. The scaling factors are used to scale the gain or attenuation of the respective signals by multipliers 44 and 144 which multiply the fundamental signals by scaling factor a and multiply the harmonic signals by scaling factor b. The scaled signals are then combined by adder 46 to produce a composite output signal of the form $aF_f'+bF_h'$, in which the relative contributions of the fundamental and harmonic components of the echo signal are adaptively controlled as a function of the received echo signal content of the two components. The contribution control characteristic is determined by the algorithm used by the comparator 42 to produce the a and b scaling factors.

The aforementioned U.S. Pat. No. 5,897,303 describes in FIG. 14 the development of images formed with blended fundamental and harmonic echo signal components. Such images take advantage of the relative characteristics of fundamental and harmonic signals at different depths and areas of the image. In general, in tissue harmonic imaging the fundamental signals are desirable at shallower depths where the distortion giving rise to harmonic components has not yet produced significant harmonic effects. Since the signal to noise ratio of fundamental signal components is likely to be greater than that of the tissue harmonic components, the image would preferably use fundamental signal components for image formation at these shallower depths. But as the transmitted wave progresses through the tissue, harmonic effects build up, and there is a transition from the predominate use of fundamental components to the predominate use of harmonic components. At intermediate image depths the use of harmonic components is preferred, as the clutter associated with fundamental signals can be eliminated. But as echoes are returned from the deepest imaging depths, the effects of depth dependent amplitude and frequency attenuation can be more significant for harmonic signals, again giving rise to the desirability of imaging with fundamental frequencies at these greater depths. The image processor could be simply pre-programmed with an algorithm that transitions from fundamental signals to harmonic signals and back to fundamental signal usage at predetermined depths which have been empirically determined. However pre-programmed transition depths would not allow a shallower depth transition to harmonic signal content when the relative quality of the funamental and harmonic signal components warrant. Preprogrammed transitions would not allow transition to harmonic signals when the relatively stronger harmonic signals from contrast agents are received at depths where tissue harmonic signals have not yet achieved the quality that mandates the transition from fundamental to harmonic imaging. The processor of FIG. 2, however, makes these transitions adaptively in accordance with the characteristics of signal content. When the comparator determines that tissue harmonic signal content has developed to a sufficient degree in comparison with the character of the fundamental signals, a transition begins as the scaling factors begin to manifest the preference for harmonic signal content. When the comparator determines that the tissue harmonic signals have degraded in comparison to the fundamental signals, the scaling factors effect a transition back to fundamental signal usage. When the nearfield tissue through which the transmitted wave travels gives rise to a more rapid buildup of harmonic content, the initial transition to harmonic signal usage will occur earlier at a shallower image depth. Similarly, when more severe attenuation occurs which causes the signal to noise ratio of the harmonic signals to fall off more rapidly, the transition to fundamental signal usage will occur earlier at a shallower depth than it might otherwise. Each new image, and indeed each new scanline, can exhibit different transition points, since the transitions are adaptively related to signal content, and not merely empirically preset in accordance with expected norms.

During harmonic contrast imaging, the harmonic echo signals returned from the contrast agents in blood vessels will in general be considerably greater than tissue harmonic signals and thus yield a very favorable comparison to the fundamental signal content at those points in the image. Thus these comparisons can result in a predominate or complete transition to the use of harmonic signals for echoes returning from blood vessels containing contrast agents. Outside of blood vessels the comparison will be between fundamental and tissue harmonic component levels and the same considerations will apply as discussed previously. The signals of a given scanline could give rise to transitions from fundamental to tissue harmonic to fundamental signal usage described above, interspersed with near instantaneous and complete transitions to harmonic signal usage whenever the beam encounters a contrast-perfused blood vessel, which quickly changes back to the tissue-based comparison as the beam passes beyond the blood vessel.

This phenomenon is illustrated in FIGS. 3 and 4. FIG. 3 illustrates an ultrasound image 100 of tissue 101 containing three blood vessel branches 104, 106, 108. One of the scanlines of the image 100 is drawn as 102. As the drawing shows, the scanline 102 initially passes through tissue, then intersects blood vessel 104. The scanline then passes through more tissue and intersects blood vessel 106. The scanline passes through tissue of increasing depth, then intersects blood vessel 108, following which the scanline passes through more tissue until it reaches the bottom (greatest depth) of the image. In this example the beam which is transmitted to produce scanline 102 is assumed to be focused at a depth between vessels 104 and 106.

FIG. 4 illustrates exemplary fundamental (Fund.) and harmonic (Har.) response curves of fundamental and harmonic echo signals returned from along scanline 102 of FIG. 3. This drawing is a generalized representation, as actual response is highly dependent upon the nature of the tissue and vessels through which the ultrasound energy passes. The fundamental response curve is seen to be significantly greater than the harmonic response at shallower depths (low Z) near the transducer, and builds in concentration as the energy transmitted by the array transducer 112 comes into focus. As the focal region is passed the Fund. response curve declines as depth dependent characteristics combine with increasingly unfocused beam conditions.

The harmonic response curve Har. begins at a very low level as tissue harmonic distortion begins to occur. Tissue harmonic energy builds rapidly with increasing depth as the transmitted energy begins to concentrate around the focal region, then declines due to depth dependent attenuation and unfocused conditions. The harmonic response shows regions 204, 206, 208 of suddenly increased response as tissue harmonic response is interrupted by contrast harmonic responses where the transmitted energy encounters the harmonic contrast agent within the blood vessels. The arrows below the drawing illustrate regions where the processor of FIG. 2 might make transitions between predominate fundamental or predominate harmonic responses. Initially the comparison between the fundamental and tissue harmonic responses would be in favor of fundamental signal usage, as indicated by the initial depth region $F_1$. When the harmonic response 204 of the contrast agent in blood vessel 104 is encountered, the comparison between the harmonic and fundamental responses causes a rapid transition to harmonic signal usage for the duration of the contrast signals. This is followed by a return to predominate fundamental signal usage $F_2$, whereafter the comparision causes a transition to tissue harmonic signal usage as the focal region is approached. The depth of tissue harmonic signal usage is seen to contain a portion during which contrast harmonic response 206 is used, which would manifest itself in the image as a region of greater contrast, e.g., brighter or differently colored as compared to the surrounding tissue harmonic image. When the tissue harmonic signal begins to degrade, a transition back to fundamental usage $F_3$ occurs. But shortly thereafter the response 208 of the contrast agent of blood vessel 108 is detected, and the processor makes a transition back to harmonic signal usage as echoes are returned from the contrast agent. After the response 208 the processor concludes with the depth region $F_4$ of fundamental signal usage. Thus, the processor is seen to adaptively respond to the different signal conditions of contrast agents, tissue harmonic signals, and fundamental signals throughout the depth of the image.

Figure 5:
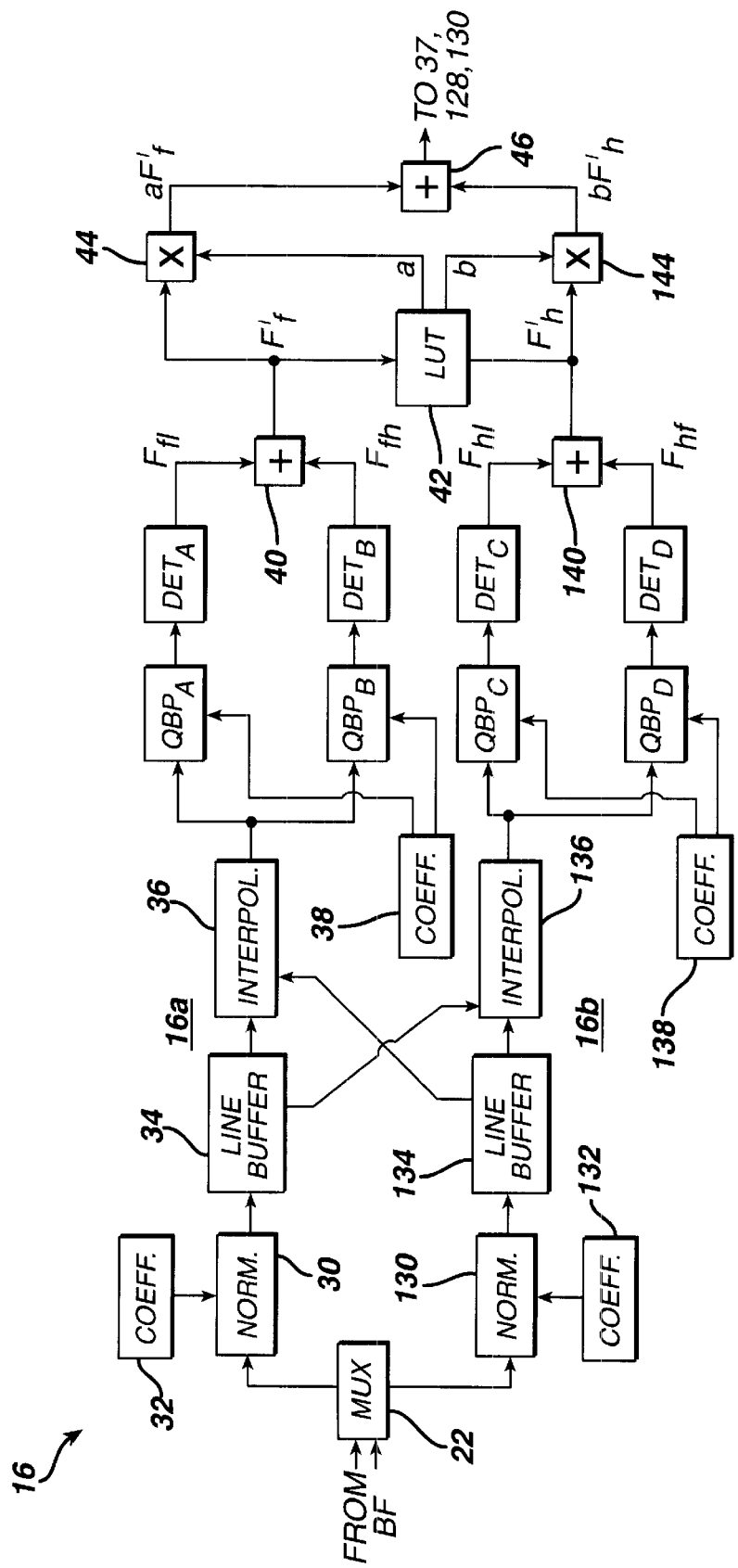
FIG. 5 illustrates in block diagram form a multi-channel digital scanline processor which blends fundamental and harmonic signals in a scanline of echo signals.

FIG. 5 illustrates a more detailed embodiment of an adaptive fundamental and harmonic imaging processor of the present invention. The processor 16 of FIG. 5 is similar to the two channel processor of FIG. 10 of the '303 patent and the multi-channel digital processor of FIG. 2 of U.S. Pat. No. 6,050,942, the contents of which are hereby incorporated by reference. Scanline echo data from the beamformer 116 is applied to a multiplexer 22. When the beamformer produces only a single scanline at a time or scanline data in a time interleaved format, only a single digital data path is needed between the beamformer and the multiplexer 22. In the illustrated embodiment, two digital data paths are shown, enabling two simultaneously generated scanlines to be coupled to the scanline processor 16 in parallel from a multi-line beamformer. The operation of the scanline processor 16 when receiving a single scanline will first be described. The multiplexer 22 applies the scanline echo data in parallel to the two channels 16a, 16b of the scanline processor illustrated in FIG. 5. Each channel of the scanline processor has a normalization stage 30,130 which multiplies the scanline data by a scale factor on a sample by sample basis to produce gain or attenuation that can vary with depth. The scale factor for each channel is provided by normalization coefficients stored in or generated by coefficient circuits 32, 132, which in a preferred embodiment are digital memories. As the multiplying coefficients are changed along the sequence of received scanline echoes, depth dependent gain or attenuation is produced.

The function of the normalization stages is two-fold. One is to compensate for a transducer aperture which expands with depth of scan. As signals from an increasing number of transducer are used with increasing depth, the magnitude of the summed beamformed signals will increase. This increase is offset by reduced gain (increased attenuation) in the normalization stage, in proportion to the rate at which channels are added to the beamforming process, so that the resultant echo sequence will be unaffected by the changing aperture.

The second function of the normalization stages is to equalize the nominal signal amplitudes of the two channels when frequency compounding is employed. The nominal signal amplitudes of the multiple passbands used for frequency compounding are desirably the same, so that the initial relative signal levels will be preserved after the passbands are summed to restore the original broad passband. But ultrasound signals are subject to depth dependent attenuation which varies with frequency, higher frequencies being more greatly attenuated with depth than lower frequencies. To account for this depth dependent attenuation the coefficients provide signal gain which increases with depth. Since frequency compounding employs different frequency passbands in the two channels of the scanline processor 16, the depth dependent gain of the two channels differs from one channel to the other. In particular, the rate of gain increase for the higher frequency passband channel is greater than that of the lower frequency passband channel. Each depth dependent gain characteristic is chosen to offset the effect of depth dependent gain for the particular frequency passband used by that channel for frequency compounding. Since higher frequencies suffer more rapid attenuation with depth than lower frequencies, the gain curve for the high frequency passband should change more rapidly than that for the low frequency passband.

After processing by the normalization stages 30,130, the echo signals in each channel 16a, 16b are coupled to line buffers 34,134. The line buffers perform several functions. First, each line buffer stores the first half aperture beamformed echo signals for synthetic aperture formation. The stored first half aperture signals are combined with the second half aperture signals as the latter are produced to form echo signals from the full synthetic aperture.

Second, the line buffers 34,134 each store a preceding scanline when the interpolators 36,136 are operating to interpolate scanline data from consecutively received scanlines. Each of the interpolators 36,136 interpolates additional scanline data between two received scanlines. Stored weighted scanline signals are cross coupled from the line buffer of one channel to the interpolator of the other channel so that two interpolated scanlines can be produced in unison, one at the output of each interpolator. In the case where the interpolators 36,136 are not active and the scanline processor 16 is processing one scanline at a time, the same sequence of scanline echoes is produced at the output of each interpolator, varying only by the different time varying gain factors of the normalization stages of the respective channels 16a, 16b.

Third, the line buffers 34,134 can each store a preceding scanline when harmonic and fundamental signals are to be separated by the pulse inversion technique. Each line buffer stores echoes of a scanline received in response to a transmit pulse of one phase or amplitude characteristic. A subsequent scanline received in response to a transmit pulse of a different phase or amplitude characteristic is combined with the stored scanline to produce a scanline of linear or non-linear echo information. The adders of the interpolators 36,136 can be used for the combining process, and will additively combine the two scanlines when nonlinear (second harmonic) signals are to be produced and will subtractively combine the two scanlines when linear (fundamental) signals are to be produced. When the interpolator 36 subtractively combines the scanline data the upper channel 16a will operate on fundamental signal information and when the interpolator 136 additively combines the scanline data the lower channel 16b will operate on harmonic signal information. When both channels are operating on the same initial scanline data, the fundamental signal components of each echo will be processed in channel 16a and the harmonic components of each echo will be processed simultaneously in channel 16b.

The echo signals in each channel are next coupled to quadrature bandpass filters (QBPs) in each channel. The quadrature bandpass filters provide three functions: band limiting the RF scanline data, producing in-phase and quadrature pairs of scanline data, and decimating the digital sample rate. Each QBP comprises two separate filters, one producing in-phase samples (I) and the other producing quadrature samples (Q), with each filter being formed by a plurality of multiplier-accumulators (MACs) implementing an FIR filter. The accumulated outputs of several MACs can be combined, and the final accumulated product comprises filtered echo data. The rate at which accumulated outputs are taken sets the decimation rate of the filter. The length of the filter is a product of the decimation rate and the number of MACs used to form the filter, which determine the number of incoming echo samples used to produce the accumulated output signal. The filter characteristic is determined by the values of the multiplying coefficients. Different sets of coefficients for different filter functions are stored in coefficient memories 38,138, which are coupled to apply selected coefficients to the multipliers of the MACs.

The coefficients for the MACs which form the I filter implement a sine function, while the coefficients for the Q filter implement a cosine function. For frequency compounding, the coefficients of the active QBPs additionally implement a sync function multiplied by a sine wave at the center frequency of the desired passband. In the instant case, when the scanline processor 16 is operating on only a single scanline at a time, $QBP_A$ in channel 16a is producing I and Q samples of the fundamental frequency scanline data in a first, low frequency passband, and $QBP_B$ in channel 16b is producing I and Q samples of the fundamental frequency scanline data in a second, higher frequency passband. Thus, the spectrum of the fundamental frequency echo signals is divided into a high frequency band $F_{fH}$ and a low frequency band $F_{fL}$. To complete the frequency compounding process, the echo data in the passbands produced by the QBP filters A and B of channel 16a is detected by combining the I and Q samples from each QBP filter in the form of $(I^2+Q^2)^{1/2}$ and the detected signals are coupled to inputs of a summer 40. The echo data in the harmonic passbands $F_{hL}$ and $F_{hH}$ produced by QBP filters C and D of channel 16b is detected by the same detection process and the detected signals are coupled to inputs of the summer 140. When the signals of the respective passbands are combined by the summers 40 and 140, respectively, the uncorrelated speckle effects of the two passbands will cancel, reducing the speckle artifacts in the images created from the signals. As explained in the '303 patent, speckle reduction is of considerable benefit when producing harmonic images, as the speckle artifact can cause dropout of signals from delicate and hard to image tissue such as the endocardium of the heart.

When the processor 16 is used with a multiline beamformer which produces multiple receive beams in response to a single transmit wave, several modes of operation are possible. One is to process one scanline through channel 16a and another simultaneously received channel through channel 16b. Alternatively the line buffers can be used to buffer scanline data, or the data from several scanlines can be processed through each channel in a time interleaved sequence. Preferably the number of channels of the processor is replicated so that multiple simultaneously received scanlines can be process in parallel. For example the line buffers in each channel can be followed by two interpolators for interpolation and pulse inversion processing, and four QBP filters in each channel so that two simultaneously received scanlines can be processed in parallel.

The speckle reduced fundamental signals $F_f'$ and the speckle reduced harmonic signals $F_h'$ are applied to inputs of a comparator which in this embodiment is formed by a look-up table (LUT) 42. The LUT is a memory device containing a two-dimensional data table. Values in the data table are accessed by using the fundamental and harmonic data as pointers to entries in the table. Thus the output of the LUT are values determined by both the fundamental and harmonic content of an echo signal. Output values of the LUT can be single digital data values which are partitioned into two parts: a scaling factor a for the fundamental signal information and a scaling factor b for the harmonic signal information. The a and b scaling factors are applied to inputs of multipliers 44 and 144 in the respective channels to produce scaled harmonic and fundamental signals of the echo data of the form $aF_f'$ and $bF_h'$. The scaled components are combined by an adder 46 to produce a speckle-reduced composite echo signal which contains fundamental and harmonic signal components adaptively proportioned in response to the relative quality of those components. Alternatively, the look-up table could directly produce image values for processors 37,128,130 which are a function of the relative values of the fundamental signals $F_f'$ and the tissue harmonic or harmonic contrast signals $F_h'$ applied to the look-up table. Moreover, since the speckle-reduced fundamental components $F_f'$ and the speckle-reduced harmonic components $F_h'$ each have their own distinctive speckle characteristics, the speckle artifact of the composite signal is further reduced when the two components are combined to form the composite signal. The output signal of the adder 46 may then be used for subsequent B mode, Doppler, tissue harmonic or contrast image processing in either a 2D or 3D format as described above.

What is claimed is:

1. An ultrasonic diagnostic imaging system comprising:
   a transducer which receives echo signals containing fundamental and tissue harmonic signal components;
   an analysis circuit coupled to receive echo signal information from said transducer which analyzes the relative fundamental and tissue harmonic signal characteristics of said echo signals; and
   a processing circuit responsive to said analysis circuit which produces echo signal information containing one of fundamental, harmonic, or a combination of fundamental and harmonic components determined in response to the relative fundamental and harmonic content of the echo signal analyzed by said analysis circuit.

2. The ultrasonic diagnostic imaging system of claim 1, wherein said transducer receives echo signals containing fundamental, tissue harmonic, and harmonic contrast agent signal components; and
   wherein said analysis circuit analyzes the relative fundamental, tissue harmonic, and harmonic contrast agent signal characteristics of said echo signals.

3. The ultrasonic diagnostic imaging system of claim 1 or 2, further comprising a detector circuit coupled to said analysis circuit which detects the relative fundamental and harmonic signal content of said echo signals.

4. The ultrasonic diagnostic imaging system of claim 3, wherein said analysis circuit acts to compare the relative quality of said fundamental and harmonic signal content of said echo signals.

5. The ultrasonic diagnostic imaging system of claim 1 or 2, wherein said processing circuit produces echo signal information containing proportions of fundamental and harmonic signal components determined in response to said analysis circuit.

6. The ultrasonic diagnostic imaging system of claim 1 or 2, further comprising a speckle reduction circuit which reduces the speckle content of at least one of said fundamental and harmonic signal components.

7. An ultrasonic diagnostic imaging system comprising:
   a transducer which receives echo signals containing fundamental and tissue harmonic signal components;
   an analysis circuit coupled to receive echo signal information from said transducer which analyzes the relative fundamental and tissue harmonic signal characteristics of said echo signals; and
   a processing circuit responsive to said analysis circuit which produces echo signal information containing fundamental and/or harmonic components determined in response to said analysis circuit,
   wherein said processing circuit produces echo signal information containing proportions of fundamental and harmonic signal components determined in response to said analysis circuit;
   wherein said analysis circuit acts to compare the relative quality of said fundamental and harmonic signal content of said echo signals; and
   wherein said processing circuit acts to increase the proportion of harmonic signal content of said echo signals relative to the fundamental signal content whenever the quality of the harmonic signal content of said echo signals exceeds a given level.

8. An ultrasonic diagnostic imaging system comprising:
   a transducer which receives echo signals containing fundamental and harmonic frequency signal components;
   a comparator circuit coupled to receive echo signal information from said transducer which compares the relative fundamental and harmonic signal characteristics of said echo signals; and
   a scaling circuit responsive to said comparator circuit which produces different proportions of fundamental and harmonic signal components of echo signals; and
   a processing circuit responsive to said scaling circuit which produces echo signal information containing proportioned fundamental and harmonic signal components.

9. The ultrasonic diagnostic imaging system of claim 8, wherein said comparator comprises a look-up table.

10. The ultrasonic diagnostic imaging system of claim 8, further comprising a separator circuit responsive to said echo signals which separates fundamental and harmonic signal components of an echo signal.

11. The ultrasonic diagnostic imaging system of claim 10, wherein said separator circuit acts to separate fundamental and harmonic signal components by pulse inversion processing.

12. The ultrasonic diagnostic imaging system of claim 10, further comprising a speckle reduction circuit responsive to said echo signals which reduces the speckle content of said echo signals.

13. The ultrasonic diagnostic imaging system of claim 12, wherein said speckle reduction circuit has an input coupled to said separator circuit and an output coupled to said comparator, wherein said speckle reduction circuit acts to reduce the speckle content of said harmonic signal components and the speckle content of said fundamental signal components.

14. An ultrasonic diagnostic imaging system comprising:

a transducer which receives echo signals containing fundamental and tissue harmonic frequency signal components;

an analysis circuit coupled to receive echo signal information from said transducer which determines the relative proportions of the fundamental and tissue harmonic signal content of an echo signal; and an adaptive proportioning circuit responsive to said analysis circuit which acts to adaptively adjust the relative proportions of fundamental and harmonic signal content of an echo signal in response to said determined proportions.

15. The ultrasonic diagnostic imaging system of claim 14, wherein said transducer receives echo signals containing fundamental, tissue harmonic, and harmonic contrast agent signal components; and wherein said analysis circuit determines the relative proportions of fundamental, tissue harmonic, and harmonic contrast agent signal content of an echo signal.

16. The ultrasonic diagnostic imaging system of claim 14 or 15, wherein said analysis circuit comprises a comparator.

17. The ultrasonic diagnostic imaging system of claim 14 or 15, wherein said analysis circuit comprises a look-up table.

18. The ultrasonic diagnostic imaging system of claim 14 or 15, wherein said analysis circuit and said adaptive proportioning circuit comprise a look-up table.

19. The ultrasonic diagnostic imaging system of claim 14 or 15, wherein said adaptive proportioning circuit comprises a multiplier responsive to said analysis circuit.

20. The ultrasonic diagnostic imaging system of claim 19, wherein said adaptive proportioning circuit further comprises an adder coupled to said multiplier which produces an echo signal with adapted proportions of fundamental and harmonic signal content.

21. The ultrasonic diagnostic imaging system of claim 14 or 15, further comprising a separator circuit responsive to said echo signals and coupled to said analysis circuit which separates fundamental and harmonic signal components of an echo signal by the process of pulse inversion.

22. The ultrasonic diagnostic imaging system of claim 21, further comprising a speckle reduction circuit which reduces the speckle content of at least one of said fundamental and harmonic signal components.

23. An ultrasonic diagnostic imaging system comprising:

a transducer which receives echo signals containing fundamental and tissue harmonic signal components;

an analysis circuit coupled to receive echo signal information from said transducer which analyzes the relative fundamental and tissue harmonic signal characteristics of said echo signals; and a processing circuit responsive to said analysis circuit which produces echo signal information containing fundamental and/or harmonic components determined in response to said analysis circuit, wherein said transducer receives echo signals containing fundamental, tissue harmonic, and harmonic contrast agent signal components;

wherein said analysis circuit analyzes the relative fundamental, tissue harmonic, and harmonic contrast agent signal characteristics of said echo signals;

wherein said processing circuit produces echo signal information containing proportions of fundamental and harmonic signal components determined in response to said analysis circuit;

wherein said analysis circuit acts to compare the relative quality of said fundamental and harmonic signal content of said echo signals; and wherein said processing circuit acts to increase the proportion of harmonic signal content of said echo signals relative to the fundamental signal content whenever the quality of the harmonic signal content of said echo signals exceeds a given level.

24. The ultrasonic diagnostic imaging system of claim 7 or 23, wherein said quality of the harmonic signal content is related to the signal to noise ratio of said harmonic signal components.

25. The ultrasonic diagnostic imaging system of claim 7 or 23, wherein said processing circuit acts to increase the proportion of harmonic signal content of said echo signals relative to the fundamental signal content whenever the quality of the harmonic signal content of said echo signals exceeds a given level, and does not act to increase the proportion of harmonic signal content of said echo signals relative to the fundamental signal content whenever the quality of the harmonic signal content of said echo signals does not exceed a given level.

* * * * *